(12) United States Patent
Kim et al.

(10) Patent No.: US 8,778,380 B2
(45) Date of Patent: Jul. 15, 2014

(54) APPARATUS FOR FABRICATING 3D SCAFFOLD FOR INSERTING IN A BODY TO REGENERATE TISSUE

(75) Inventors: Wan-Doo Kim, Daejeon (KR); Jun Hee Lee, Daejeon (KR); Su-A Park, Daejeon (KR)

(73) Assignee: Intellectual Discovery Co., Ltd., Seoul (KR)

( * ) Notice: Subject to any disclaimer, the term of this patent is extended or adjusted under 35 U.S.C. 154(b) by 491 days.

(21) Appl. No.: 13/116,465

(22) Filed: May 26, 2011

(65) Prior Publication Data

US 2011/0287122 A1 Nov. 24, 2011

Related U.S. Application Data

(63) Continuation-in-part of application No. 11/617,851, filed on Dec. 29, 2006, now abandoned.

(30) Foreign Application Priority Data

Apr. 26, 2006 (KR) .................. 10-2006-0037521

(51) Int. Cl.
| | |
|---|---|
| *A61F 2/02* | (2006.01) |
| *A61K 9/00* | (2006.01) |
| *C12M 1/00* | (2006.01) |
| *C12N 5/07* | (2010.01) |
| *B28B 1/00* | (2006.01) |
| *C12N 5/00* | (2006.01) |

(52) U.S. Cl.
CPC .......... *C12N 5/0062* (2013.01); *C12N 2533/40* (2013.01)
USPC ..... 424/423; 424/400; 435/283.1; 435/284.1; 435/395; 425/375

(58) Field of Classification Search
None
See application file for complete search history.

(56) References Cited

U.S. PATENT DOCUMENTS

| | | | | |
|---|---|---|---|---|
| 4,498,139 | A | * | 2/1985 | Malinovsky .................. 345/168 |
| 7,625,198 | B2 | | 12/2009 | Lipson et al. |
| 7,658,603 | B2 | | 2/2010 | Medina et al. |
| 7,661,541 | B2 | | 2/2010 | Dao et al. |
| 7,759,082 | B2 | | 7/2010 | Bowlin et al. |

* cited by examiner

*Primary Examiner* — David M Naff
(74) *Attorney, Agent, or Firm* — Fox Rothschild LLP

(57) ABSTRACT

An apparatus for fabricating a 3D scaffold includes: a plotter generating a microfiber structure; an electrospinning unit installed to be adjacent to the plotter along a first direction and spinning nanofiber in an internal space or on a surface of the microfiber structure to form a nanofiber web; a collection table reciprocating a lower portion of the plotter and that of the electrospinning unit along the first direction to allow the microfiber structure to be stacked thereon by the plotter and allow the nanofiber web to be formed thereon by the electrospinning unit; and a first guide rail allowing the collection table to be mounted thereon and guiding the collection table mounted thereon to reciprocate along the first direction.

7 Claims, 7 Drawing Sheets

(a) Normal 3D scaffold (b) Hierachical structured 3D scaffold (a) Normal 3D scaffold (b) Hierachical structured 3D scaffold (c) MTT assay

US 8,778,380 B2

APPARATUS FOR FABRICATING 3D SCAFFOLD FOR INSERTING IN A BODY TO REGENERATE TISSUE

CROSS-REFERENCE TO RELATED APPLICATION

This application is a continuation in part of U.S. application Ser. No. 11/617,851, by KIM et al., filed Dec. 29, 2006, which claims priority to and the benefit of Korean Patent Application No. 10-2006-0037521 filed in the Korean Intellectual Property Office on Apr. 26, 2006, the entire contents of now abandoned which are incorporated herein by reference.

BACKGROUND OF THE INVENTION (a) Field of the Invention

The present invention relates to an apparatus for fabricating a 3D (three-dimensional) scaffold and a fabrication method thereof, and more particularly, to a fabrication apparatus for forming a scaffold for tissue regeneration and a fabrication method using the same.

(b) Description of the Related Art

When an organ or tissue in a human body is damaged, a cell, a medical scaffold, or the like, is provided to effectively regenerate the damaged organ or tissue. The tissue regeneration scaffold is required to have such physiological activities that it is physically stable at an implanted part and can adjust regenerative efficacy, and also, it is to be decomposed in a living body after new tissue is formed, and in this case, a degradation product should not have virulence.

Such a tissue regeneration scaffold is fabricated as a sponge-type scaffold using a polymer having a certain strength and shape or as a nanofiber- or gel-type scaffold having a matrix form. A technique in which a cell culture scaffold is transplanted to regenerate tissue in a living body by using self-healing power is called regenerative medicine or tissue engineering.

A method of regenerating articula cartilage is an example of tissue technology, in forms a prosthesis using a cartilage cell as a scaffold is formed, and the prosthesis is transplanted to a damaged part to thus allow the cartilage cell to be regenerated. The prosthesis is formed as a scaffold configured to have a 3D shape by using a cartilage cell, or the like, as a seed.

In order to form such a scaffold having a 3D shape, a rapid prototyping scheme, and in particular, a laminated (or stacked) rapid prototyping scheme, is used.

The laminated rapid prototyping scheme is used to process a divided sheet into a plurality of layers and sequentially stacking them to obtain a prototype having a desired shape. That is, a 3D shape modeled through a CAD system is divided into a plurality of sheets having a certain thickness, changing them into slice data, prototyping a plate-shaped sheet on the basis of the slice data, and stacking them to form a prototype.

The conventional 3D scaffold fabrication method, however, has shortcomings in that, since a 3D shape is modeled and divided into a plurality of sheets having a certain thickness and the plurality of divided sheets are sequentially stacked to form a prototype, much time is required for dividing and stacking the sheets.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide an apparatus for fabricating a 3D scaffold having advantages of fabricating a 3D scaffold within a short time and forming a fine scaffold for proliferating cells by forming a 3D microfiber structure through a plotter scheme and forming a nanofiber web in the structure through electrospinning.

An exemplary embodiment of the present invention provides an apparatus for fabricating a 3D scaffold including: a plotter generating a microfiber structure; an electrospinning unit installed to be adjacent to the plotter along a first direction and spinning nanofiber in an internal space or on a surface of the microfiber structure to form a nanofiber web; a collection table reciprocating a lower portion of the plotter and that of the electrospinning unit along the first direction to allow the microfiber structure to be stacked thereon by the plotter and allow the nanofiber web to be formed thereon by the electrospinning unit; and a first guide rail allowing the collection table to be mounted thereon and guiding the collection table mounted thereon to reciprocate along the first direction.

The apparatus may further include a back frame on which the plotter and the electrospinning unit are mounted together and integrally supported.

The apparatus may further include a second guide rail allowing the first guide rail to be mounted thereon and guiding the first guide rail along a second direction that crosses the first direction.

The plotter may be mounted on a first support member that can reciprocate along a third direction that crosses the first and second directions, and the electrospinning unit may be mounted on a second support member that can reciprocate along the third direction. A separator may be installed between the first and second support members.

The plotter may include a first solution storage tank storing a biopolymer solution, and a plotter nozzle discharging a solution supplied from the first solution storage tank.

The electrospinning unit may include a second solution storage tank storing a biopolymer solution, and an electrospinning nozzle electrospinning a solution supplied from the second solution storage tank. The apparatus may further include a voltage generator connected to the electrospinning nozzle and the collection table and applying a voltage between the electrospinning nozzle and the collection table.

In another embodiment, the electrospinning nozzle may be formed to be tilted at a predetermined angle with reference to a perpendicular direction. A tip of the electrospinning nozzle may be positioned at a predetermined distance in a horizontal direction from the 3D scaffold.

Another embodiment of the present invention provides a method for fabricating a 3D scaffold, including: forming a microfiber structure including a plurality of stacked unit layers on the basis of 3D coordinate data generated by modeling a 3D shape; and forming a nanofiber web between the plurality of unit layers of the microfiber structure.

The forming of the microfiber structure may include a first stage of forming unit layers of the microfiber structure, the forming of the nanofiber web may include a second stage of forming a nanofiber web on the surface of the unit layers of the microfiber structure, and the first and second stages may be repeatedly performed at least one or more times.

The forming of the microfiber structure may include a first stage of stacking a plurality of unit layers to form the microfiber structure, the forming of the nanofiber web may include a second stage of forming a nanofiber web on the surface of the microfiber structure, and the first and second stages may be repeatedly performed at least one or more times.

The forming of the microfiber structure may include dispensing the biopolymer solution by using the plotter while relatively moving the collection table with respect to the plotter on the basis of the 3D coordinate data generated by modeling a 3D shape.

The forming of the nanofiber web may include moving the collection table with the microfiber structure formed thereon to position the collection table such that it corresponds to the electrospinning unit, and electrospinning the biopolymer solution by using the electrospinning unit.

The forming of the microfiber structure and the forming of the nanofiber web may be repeatedly performed at least one or more times, while reciprocating the collection table from the plotter to the electrospinning unit or from the electrospinning unit to the plotter.

DETAILED DESCRIPTION OF THE EMBODIMENTS

Figure 1:
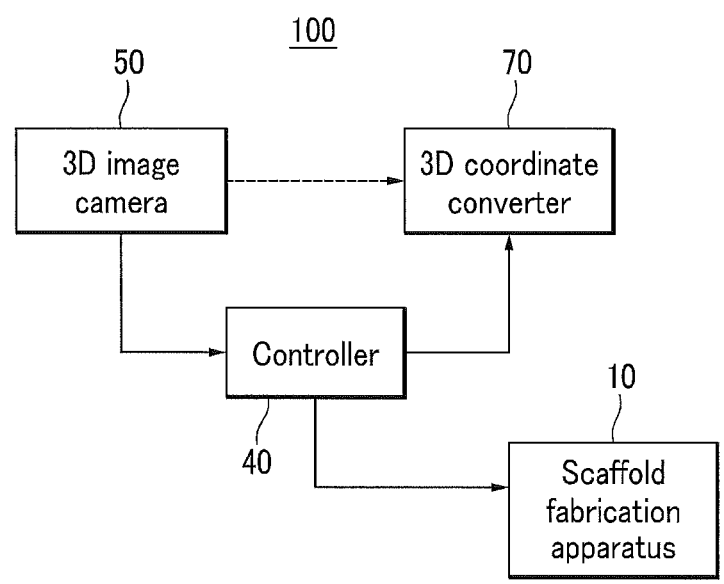
FIG. 1 is a schematic block diagram of a system for fabricating a 3D scaffold according to a first exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a schematic block diagram of a system 100 for fabricating a 3D scaffold according to a first exemplary embodiment of the present invention.

With reference to FIG. 1, the 3D scaffold fabrication system 100 according to the first exemplary embodiment of the present invention includes a 3D image camera 50, a 3D coordinate converter 70, a 3D scaffold fabrication apparatus 10, and a controller 40.

The 3D image camera 50 serves to capture an image of, for example, a bone of a human body three-dimensionally to obtain a 3D image, and the 3D coordinate converter 70 serves to model the obtained 3D image and digitize a stereoscopic distance to digital coordinate data, and convert the same. The 3D scaffold fabrication apparatus 10 serves to receive the coordinate data from the 3D coordinate converter 70 and plot a 3D scaffold.

The controller 40, which may be configured, for example, as a control computer, is connected to the 3D coordinate converter 70 and the 3D scaffold fabrication apparatus 10 to receive the digital coordinate data from the 3D coordinate converter 70 and transmit the received digital coordinate data to the 3D scaffold fabrication apparatus 10 to control operation of the 3D scaffold fabrication apparatus 10.

The 3D scaffold fabrication system 100 may be configured such that the 3D image camera 50, the 3D coordinate converter 70, the controller 40, and the 3D scaffold fabrication apparatus 10 are sequentially connected to sequentially transmit and receive data.

In another embodiment, the 3D scaffold fabrication system may be configured such that the 3D image camera 50, the 3D coordinate converter 70, and the 3D scaffold fabrication apparatus 10 are all connected to the controller 40, and the controller 40 controls the respective elements. In this configuration, a 3D image of the 3D image camera 50 is transmitted to the controller 40, and then the controller 40 transmits the received 3D image to the 3D coordinate converter 70, receives converted coordinate data from the 3D coordinate converter 70, and inputs the received converted coordinate data to a driving program of the controller 40 to drive the 3D scaffold fabrication apparatus 10.

Hereinafter, the 3D scaffold fabrication apparatus 10 according to the present exemplary embodiment will be described with reference to FIGS. 2 and 3.

Figure 2:
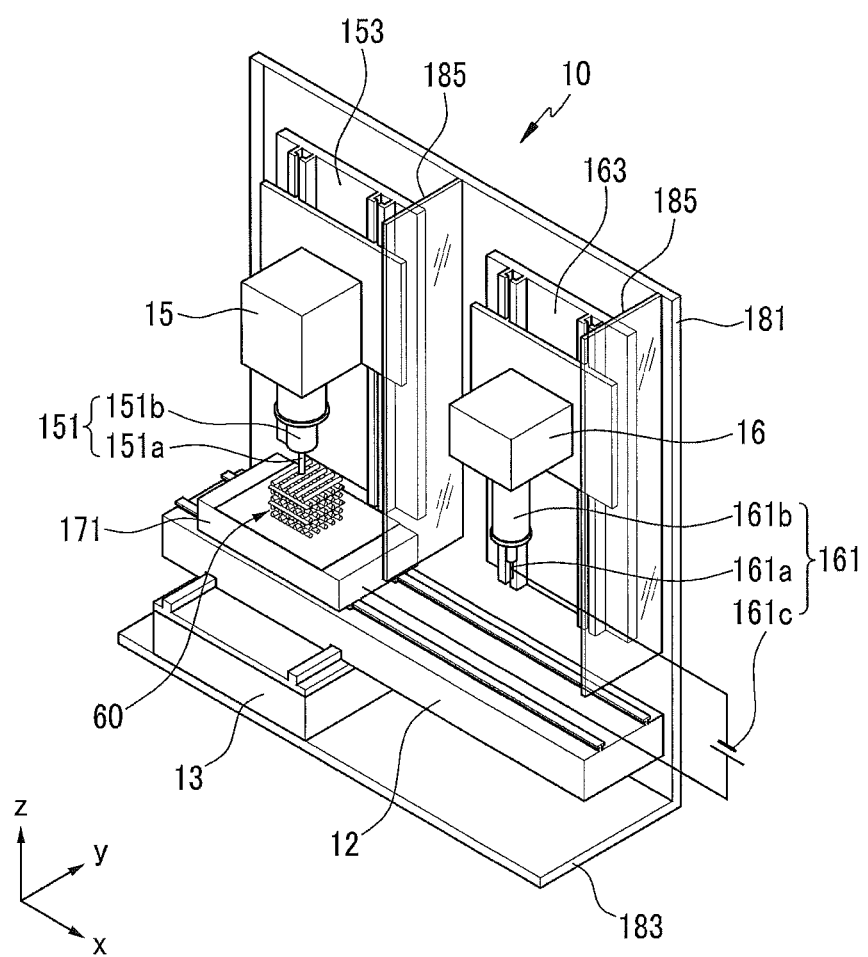
FIG. 2 is a perspective view of a 3D scaffold fabrication apparatus according to the first exemplary embodiment of the present invention.
Figure 3:
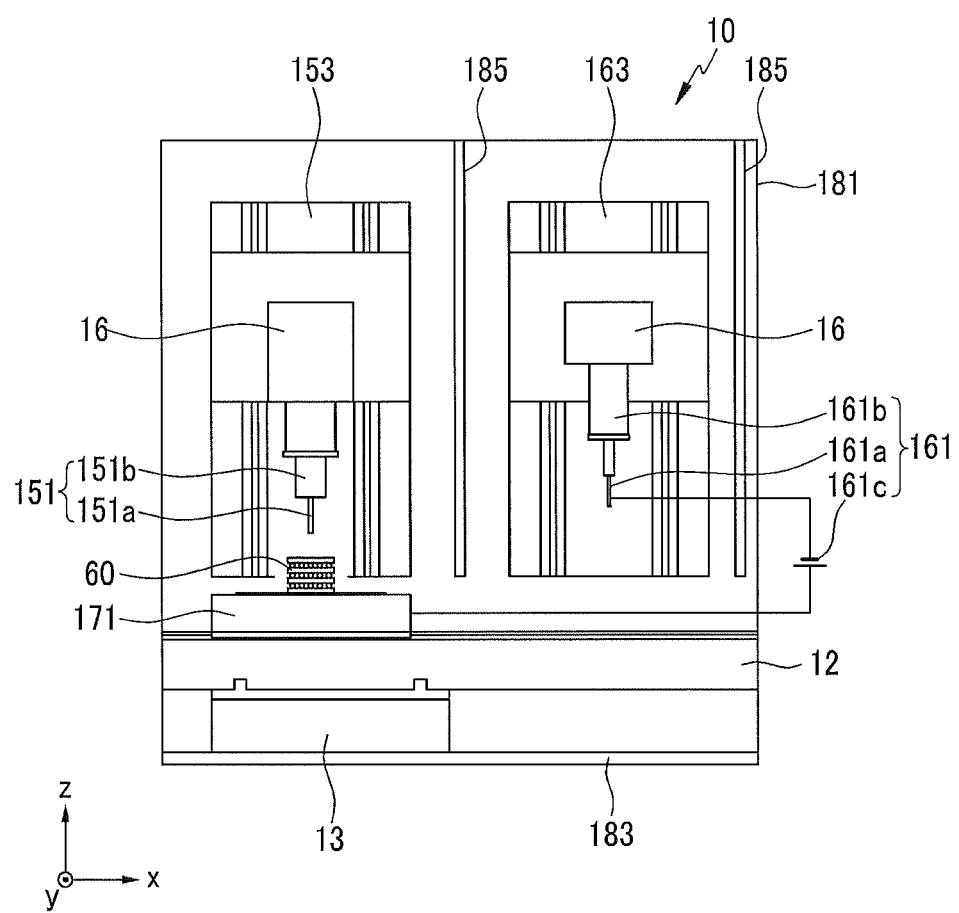
FIG. 3 is a front view of the 3D scaffold fabrication apparatus according to the first exemplary embodiment of the present invention.

FIG. 2 is a perspective view of the 3D scaffold fabrication apparatus 10 according to the first exemplary embodiment of the present invention, and FIG. 3 is a front view of the 3D scaffold fabrication apparatus 10 according to the first exemplary embodiment of the present invention.

With reference to FIGS. 2 and 3, the 3D scaffold fabrication apparatus 10 includes a plotter 151 for generating a microfiber structure and an electrospinning unit 161 for forming a nanofiber web. The electrospinning unit 161 is installed to be adjacent to the plotter 151 along a first direction (i.e., an x-axis direction in FIG. 2), and electrospins nanofiber in an internal space or on a surface of the microfiber structure to form a nanofiber web. Thus, a scaffold 60 (See FIG. 5) fabricated through the 3D scaffold fabrication apparatus 10 according to the present exemplary embodiment is configured as the nanofiber web that is formed at the microfiber structure.

A collection table 171 is positioned at a lower side of the plotter 151 and the electrospinning unit 161. The collection table 171, reciprocating along the first direction, is selectively positioned at the lower side of the plotter 151 or the electrospinning unit 161. Thus, when the collection table 171 is positioned below the plotter 151, the microfiber structure is stacked on the collection table 171 by the plotter 151, and when the collection table 171 is positioned below the electrospinning unit 161, the nanofiber structure is stacked on the collection table 171 by the electrospinning unit 161.

The collection table 171 is mounted on a first guide rail 12 so as to be guided to reciprocate along the first direction. The first guide rail 12 is mounted on a second guide rail 13 so as to be guided to reciprocate along a second direction (i.e., a y-axis direction in FIG. 2) that crosses the first direction. That is, the collection table 171 and the first guide rail 12 may be connected to the controller 40 and movable along x axis and y axis according to input coordinates, and accordingly, the collection table 171 may move relatively with respect to the plotter 151 so as to be placed at a position on a plane. The second guide rail 13 may be supportedly mounted on a base frame 183. The operation of the first guide rail 12 and the collection table 171 may be coupled and controlled with an electronic or mechanical driving means (not shown). The first guide rail 12 and the collection table 171 may be configured with a stage transporting means known to the public.

Meanwhile, the plotter 151 and the electrospinning unit 161 are mounted together on a back frame 181 and integrally supported by the back frame 181. A first support member 15 and a second support member 16, which can reciprocate along a third direction (i.e., a z-axis direction in FIG. 2) that crosses the first and second directions, are installed to be adjacent in the first direction. The plotter 151 is mounted at the first support member 15, and the electrospinning unit 161 is mounted at the second support member 16. A separator 185 is installed between the first and second support members 15 and 16 to prevent a biopolymer solution electrospun from the electrospinning unit 161 from spreading to a working area (or an operation area) of the plotter 151 mounted at the first support member 15. As shown in FIG. 2, a pair of separators 185 may be formed at the left and right of the second support member 16.

The plotter 151 includes a first solution storage tank 151*b* storing the biopolymer solution and a plotter nozzle 151*a* for discharging a solution supplied from the first solution storage tank 151*b*. The electrospinning unit 161 includes a second solution storage tank 161*b* storing the biopolymer solution and an electrospinning nozzle 161*a* electrospinning a solution supplied from the second solution storage tank 161*b*. A voltage generator 161*c* is connected to the electrospinning nozzle 161 and the collection table 171 to apply a voltage between the electrospinning nozzle 161 and the collection table 171. The biopolymer solution electrospun from the electrospinning nozzle 161*a* by the applied voltage may be finely spun in the form of nanofiber through electrospinning. In this embodiment, the electrospinning nozzle 161*a* is directed vertically downward (i.e., a z-axis direction in FIG. 2)

In the thusly configured 3D scaffold fabrication apparatus 10, the plotter 151, the electrospinning unit 161, and the collection table 171 are relatively moved under the control of the controller 40 to generate the 3D scaffold 60, and the generated 3D scaffold 60 may be inserted into a human body so as to be used to regenerate tissue.

Figure 4:
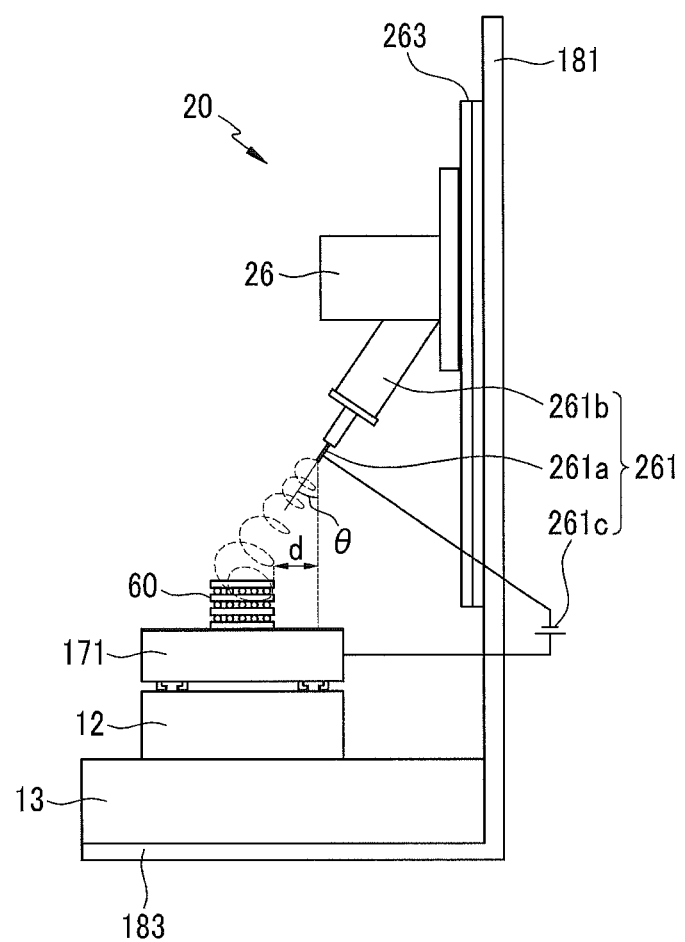
FIG. 4 is a perspective view of a 3D scaffold fabrication apparatus according to the second exemplary embodiment of the present invention.

FIG. 4 is a perspective view of a 3D scaffold fabrication apparatus according to the second exemplary embodiment of the present invention.

With reference to FIG. 4, the 3D scaffold fabrication apparatus 20 includes a plotter 251 for generating a microfiber structure and an electrospinning unit 261 for forming a nanofiber web. The electrospinning unit 261 is installed to be adjacent to the plotter 251 along a first direction (i.e., an x-axis direction in FIG. 4), and electrospins nanofiber in an internal space or on a surface of the microfiber structure to form a nanofiber web. Thus, a scaffold 60 fabricated through the 3D scaffold fabrication apparatus 20 according to the present exemplary embodiment is configured as the nanofiber web that is formed at the microfiber structure.

The electrospinning unit 261 includes a second solution storage tank 261*b* storing the biopolymer solution and an electrospinning nozzle 261*a* electrospinning a solution supplied from the second solution storage tank 261*b*. In this embodiment, the electrospinning nozzle 261*a* is formed to be tilted at a predetermined angle θ with reference to a perpendicular direction (i.e., a z-axis direction in FIG. 4). A tip of the electrospinning nozzle 261*a* is positioned at a predetermined distance d in a horizontal direction from the 3D scaffold 60. The angle θ may be in a range from 5 to 70 degree with reference to the perpendicular direction, preferably, may be in a range from 30 to 45 degree with reference to the perpendicular direction. The second solution storage tank 261*b* may be formed to be tilted at the angle θ of the electrospinning nozzle 261*a*.

With tilting the electrospinning nozzle 261*a*, the solution drops, which can flow out from the tip of the electrospinning nozzle 261*a*, may not fall directly over the 3D scaffold 60, while electrospinning the biopolymer solution to the 3D scaffold 60.

Elements that are not described in the above description about the 3D scaffold fabrication apparatus 20 may be configured as same as the 3D scaffold fabrication apparatus 10 according to the first embodiment.

Hereinafter, a method for fabricating a scaffold by using the 3D scaffold fabrication system 100 will be described.

Figure 5:
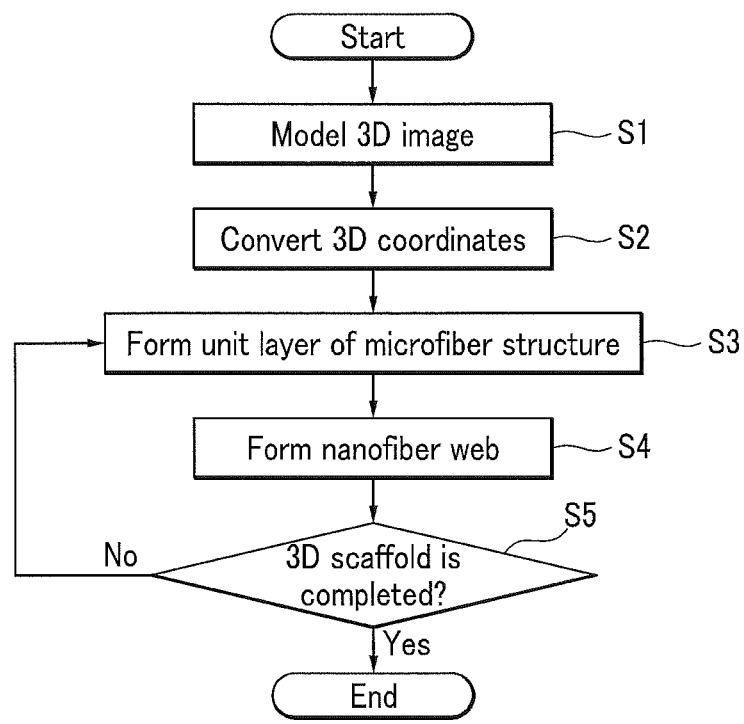
FIG. 5 is a flowchart illustrating the process of a method for fabricating a 3D scaffold according to the third exemplary embodiment of the present invention.
Figure 6:
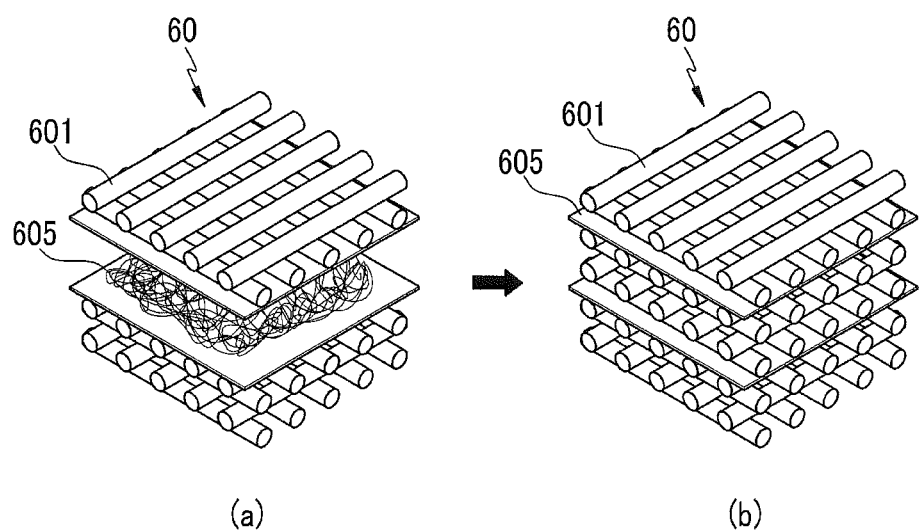
FIG. 6 is a schematic perspective view of a 3D scaffold fabricated according to the fabrication method illustrated in FIG. 5.

FIG. 5 is a flowchart illustrating the process of a method for fabricating a 3D scaffold according to the third exemplary embodiment of the present invention, and FIG. 6 is a schematic perspective view of a 3D scaffold fabricated according to the fabrication method illustrated in FIG. 5.

The method for fabricating a 3D scaffold according to the present exemplary embodiment includes obtaining and modeling a 3D image (S1), converting coordinates of the modeled 3D image (S2), forming a microfiber structure 601 including a plurality of stacked unit layers based on 3D coordinate data, and forming a nanofiber web 605 between the plurality of unit layers of the microfiber structure 601.

The step of forming the microfiber structure 601 includes a first stage (S3) of forming a unit layer of the microfiber structure 601, and the forming of the nanofiber web 605 includes a second stage (S4) of forming the nanofiber web 605 on the surface of the unit layer of the microfiber structure 601. The unit layers of the microfiber structure 601 and the nanofiber web 605 are alternately stacked by repeatedly performing the first and second stages at least one or more times, and in this case, the nanofiber webs 605 are formed between the unit layers of the microfiber structure 601.

In another embodiment, in the first stage of forming the unit layer of the microfiber structure 601, the microfiber structure 601 may be formed by stacking a plurality of unit layers, and the nanofiber web 605 may be formed on the surface of the thusly formed microfiber structure 601. The plurality of unit layers and the nanofiber web 605 are alternately stacked by repeatedly performing the stages one or more times, and the nanofiber web 605 is formed between the plurality of unit layers of the microfiber structure 601.

The method for fabricating a 3D scaffold by using the 3D scaffold fabrication apparatus 10 as described above will now be described in more detail.

First, the forming of the microfiber structure 601 includes dispensing the biopolymer solution by using the plotter 151 while relatively moving the collection table 171 with respect to the plotter 151 on the basis of the 3D coordinate data generated by modeling a 3D form.

The forming of the nanofiber web 605 includes moving the collection table 171 with the microfiber structure 601 formed thereon to position the collection table 171 such that it corresponds to the electrospinning unit 161, and finely spinning the biopolymer solution in the form of nanofiber by using the electrospinning unit 161.

The 3D scaffold 60 having the nanofiber web 605 formed between the unit layers of the microfiber structure 601 can be fabricated by repeatedly performing the step of forming the microfiber structure 601 and the step of forming the nanofiber web 605 at least one or more times by reciprocating the collection table 171 between the plotter 151 and the electrospinning unit 161 (that is, from the plotter 151 to the electrospinning unit 161, or vice versa).

[Exemplary Experiment]

Biodegradable poly(ε-caprolactone) (PCL, Mw=80,000) resin was transferred to the melting cartilage, which is similar to a mini-single screw extruder. The melted polymer was plotted with a 250 μm dispensing needle tip, laid down layer by layer. To complete one layer, the perpendicular strands were first plotted and then the PCL micro/nanofibers were electrospun on top. The plotted layers adhered to the electrospun fibers and the previously plotted layer. The geometrical size of fabricated PCL scaffolds was approximately 10×10×5 mm$^3$. The thickness and diameter of the deposited spun fibers and diameter of spun fibers were 10~25 μm and 700~2,000 nm, respectively. The electrospun PCL solution was prepared by dissolving 2.4 g of PCL in 30 g of a solvent mixture composed of methylene chloride (MC) and dimethylformamide (DMF). The solvents were used in MC/DMF wt.-% ratios of 80/20. The PCL solution was prepared at 8 wt.-% in the solvent, and the electrical conductivity of the solution was 51 μs/m. The polymer solution was placed in a 20 ml glass syringe with a G-20 needle. The flow rate of the polymer solution was controlled using a syringe pump. A power supply was used to provide a high electrical field. The flow rates of the plotting system and electrospinning process were 250 mm/min and 3 ml/h, respectively.

Figure 7:
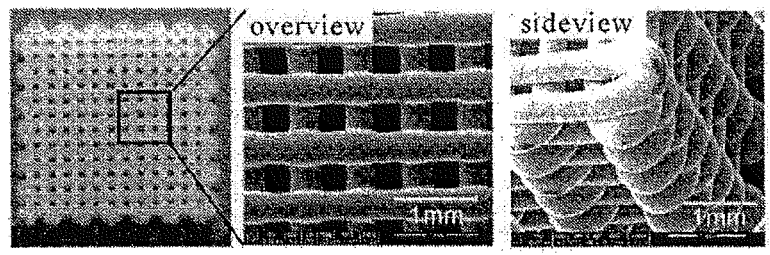
FIG. 7 shows SEM images comparatively showing an image (a) of a PCL (polycaprolactone) scaffold fabricated according to a conventional method and an image (b) of a PCL scaffold fabricated according to the fabrication method according to the third exemplary embodiment of the present invention.
Figure 7:
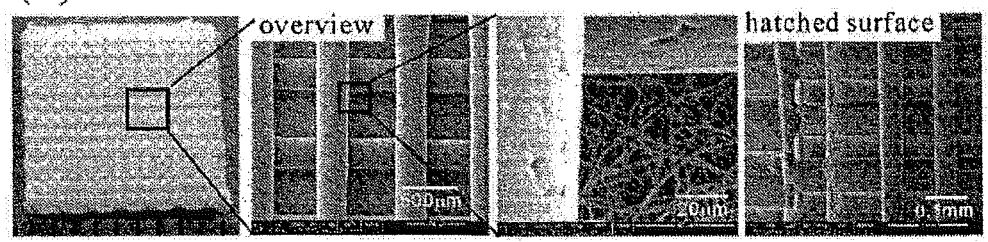

FIG. 7 shows SEM images comparatively showing an image (a) of a PCL (polycaprolactone) scaffold fabricated according to a conventional method and an image (b) of a PCL scaffold fabricated according to the fabrication method according to the third exemplary embodiment of the present invention.

FIG. 7 (b) clearly indicates that the layers of electrospun micro/nanofibers were located between the layers of dispensed strands. The strand size and fiber diameters were 250~270 μm and 700~3,000 nm, respectively. The strands were plotted at a melting temperature of 100° C. (dynamic viscosity=4×10$^4$ poise at 100 rad/s), and the moving speed of the plotter head was 220 mm/min. The ambient temperature was 25° C.

Figure 8:
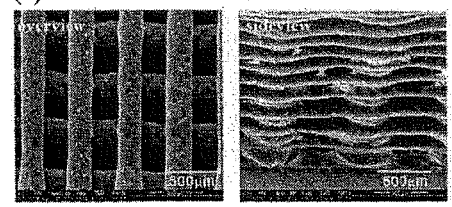
FIG. 8 shows SEM images (a) of chondrocytes attached to the 3D scaffold fabricated according to the conventional method, a SEM image (b) of chondrocytes attached to the 3D scaffold fabricated according to the third embodiment of the present invention, and an MTT assay graph (c) showing initial cell attachment and proliferation of chondrocytes.
Figure 8:
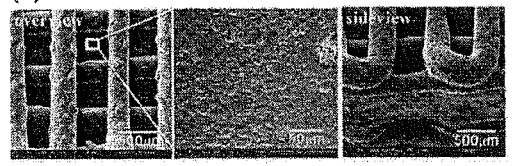
Figure 8:
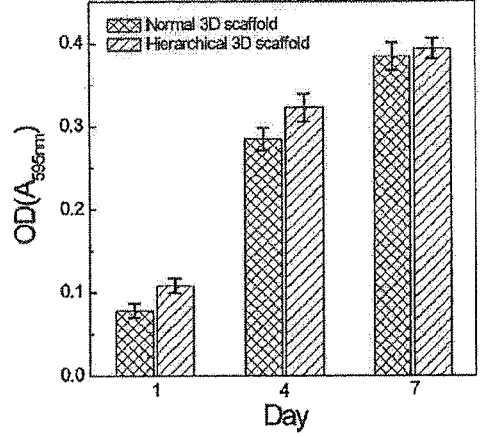

FIG. 8 shows a SEM image (a) of chondrocytes attached to the 3D scaffold fabricated according to a conventional method, a SEM image (b) of chondrocytes attached to the 3D scaffold fabricated according to the third embodiment of the present invention, and an MTT assay graph (c) showing an initial cell attachment and proliferation of chondrocytes.

To evaluate the effects of the 3D hybrid scaffold on cell proliferation, chondrocytes were embedded in both the normal 3D structure (FIG. 8 (a)) and the hierarchical 3D scaffold (FIG. 8 (b)). Generally, the micro/nanoscale of the fibrous structure promotes cell growth due to its high surface area-to-volume ratio. As shown in FIG. 8(b), chondrocytes spread out much better on the nanofiber webs inserted between plotted strands than on the normal strand structure. The embedded cells were fully spread on the nanofiber layer between strands in the hybrid scaffold, while for the normal 3D scaffold the cells were not packed in the pores between strands. As shown in FIG. 8(c), we measured chondrocyte proliferation on the 3D scaffolds using the MTT assay. These results indicate that the nanofiber webs in the hybrid 3D scaffold can provide a good matrix to maintain adhesion of the injected cells. This encourages rapid and stable tissue formation through cell attachment, growth and proliferation.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for fabricating a 3D scaffold that can be inserted into a human body so as to be used to regenerate tissue, the apparatus comprising:
   a back frame;
   a plotter supported by the back frame for generating a microfiber structure;
   an electrospinning unit supported by the back frame and adjacent to the plotter along a first direction for spinning nanofiber in an internal space or on a surface of the microfiber structure to form a nanofiber web;
   a collection table for reciprocating below a lower portion of the plotter and below the lower portion of the electrospinning unit along the first direction to allow the microfiber structure to be formed on the collection table by the plotter and allow the nanofiber web to be formed on the collection table by the electrospinning unit;
   a first guide rail allowing the collection table to be mounted thereon and guiding the collection table mounted thereon to reciprocate along the first direction: and
   a second guide rail having the first guide rail mounted thereon for guiding the first guide rail along a second direction that crosses the first direction.

2. The apparatus of claim 1, wherein the plotter is mounted on a first support member attached to the back frame such that the plotter can reciprocate along a third direction that crosses the first and second directions, and the electrospinning unit is mounted on a second support member attached to the back frame such that the electrospinning unit can reciprocate along the third direction.

3. The apparatus of claim 2, wherein a separator is installed between the first and second support members.

4. The apparatus of claim 1, wherein the plotter comprises:
   a first solution storage tank for storing a biopolymer solution; and a plotter nozzle for discharging a solution supplied from the first solution storage tank.

5. The apparatus of claim 1, wherein the electrospinning unit comprises:
   a second solution storage tank for storing a biopolymer solution; and an electrospinning nozzle for electrospinning a solution supplied from the second solution storage tank.

6. The apparatus of claim 5, wherein the electrospinning nozzle is formed to be tilted at a predetermined angle with reference to a perpendicular direction.

7. The apparatus of claim 5, further comprising
   a voltage generator connected to the electrospinning nozzle and the collection table for applying a voltage between the electrospinning nozzle and the collection table.

* * * * *